United States Patent [19]
Stevenson

[11] Patent Number: 5,239,176
[45] Date of Patent: Aug. 24, 1993

[54] TAPERED OPTICAL FIBER SENSING ATTENUATED TOTAL REFLECTANCE

[75] Inventor: William A. Stevenson, Concord, Mass.

[73] Assignee: Foster-Miller, Inc., Waltham, Mass.

[21] Appl. No.: 771,157

[22] Filed: Oct. 3, 1991

[51] Int. Cl.⁵ .................. H01J 5/16; G01N 15/06; G01N 21/41
[52] U.S. Cl. .................. 250/227.25; 250/227.21; 250/905; 385/12; 356/133
[58] Field of Search ............... 385/12; 250/227.25, 250/227.21, 573, 574, 227.11, 576, 903-907; 356/133, 441, 442, 73.1

[56] References Cited

U.S. PATENT DOCUMENTS

| | | | |
|---|---|---|---|
| 4,403,826 | 9/1983 | Presby | 385/12 |
| 4,447,546 | 5/1984 | Hirschfeld . | |
| 4,451,116 | 5/1984 | Pinnow et al. . | |
| 4,595,833 | 6/1986 | Sting . | |
| 4,671,938 | 6/1987 | Cook . | |
| 4,788,436 | 11/1988 | Koechner | 385/12 |
| 4,798,954 | 1/1989 | Stevenson . | |
| 4,827,121 | 5/1989 | Vidrine, Jr. et al. | 356/133 |
| 4,852,967 | 8/1989 | Cook et al. . | |
| 4,893,894 | 1/1990 | Caimi | 385/12 |
| 4,981,338 | 1/1991 | Bobb et al. . | |
| 4,988,863 | 1/1991 | Bobb et al. | 250/227.25 |
| 5,000,901 | 3/1991 | Iyer et al. . | |
| 5,044,723 | 9/1991 | MacDonald | 385/12 |
| 5,070,243 | 12/1991 | Bornstein et al. | 356/133 |

FOREIGN PATENT DOCUMENTS

| | | | |
|---|---|---|---|
| 417700A2 | 9/1990 | European Pat. Off. . | |
| 0253446 | 11/1986 | Japan | 356/133 |
| 0047531 | 3/1987 | Japan | 385/12 |
| 2236145 | 9/1990 | Japan | 356/133 |

OTHER PUBLICATIONS

Compton et al., In Situ FT-IR Analysis of a Composite Curing Reaction Using a Mid-Infrared Transmitting Optical Fiber, *Applied Spectroscopy*, vol. 42, No. 6, pp. 972-979 (1988).

Druy et al., Fourier Transform Infrared (FTIR) Fiber Optic Monitoring of Composite During Cure, *Fiber Optic Smart Structures and Skins II*, SPIE, vol. 1170, pp. 150-159 (1989).

Druy et al., In-Situ Characterization of Resin Chemistry With Infrared Transmitting Optical Fibers and Infrared Spectroscopy, *Applied Spectroscopy*, SPIE vol. 1437, pp. 66-74 (1991).

Young et al., "FTIR Characterization of Advanced Materials", 31st, Nat. Sample Symp., Apr. 1986, pp. 1-15.

*Primary Examiner*—David C. Nelms
*Assistant Examiner*—Michael Messinger
*Attorney, Agent, or Firm*—Fish & Richardson

[57] ABSTRACT

A radiation transmission fiber for spectroscopic monitoring includes a transmission portion and a sensor portion; the transmission and sensor portions have a continuous core portion and continuous cladding over the core portion throughout the transmission and sensor portions; the sensor portion of the core is of smaller diameter than the transmission portion(s) and is connected to the transmission portion(s) by a conical transition portion(s); and the cladding in the transmission portion is of greater thickness than the cladding in the sensor region.

28 Claims, 2 Drawing Sheets

TAPERED OPTICAL FIBER SENSING ATTENUATED TOTAL REFLECTANCE

This invention relates to spectroscopic technology, and more particularly to technology for analyzing material using optical fiber-attenuated total reflectance technology.

Spectroscopy is frequently employed in qualitative and quantitive analysis of materials. Infrared radiation detection techniques are frequently advantageous over spectroscopic techniques using radiation of shorter wavelengths, such as visible or ultraviolet light, as organic and biological materials have characteristic strong and relatively narrow absorption peaks in the infrared region. Fourier transform infrared (FTIR) spectroscopic monitoring is useful in spectroscopy, as discussed, for example, in the Stevenson U.S. Pat. No. 4,798,954, Vidrine U.S. Pat. No. 4,827,121, and Cook U.S. Pat. No. 4,852,967. The material being analyzed or monitored may be gaseous, liquid or solid.

This invention relates to the use of an optical fiber as a multiple internal reflection (MIR) sensor and more particularly to the technology of using optical fibers as MIR sensors for performing both emission spectroscopy and absorption spectroscopic measurements of highly absorbing or highly scattering material, a technique sometimes referred to as evanescent wave spectroscopy. Such technology has used an unclad fiber portion that is disposed in a liquid, solid or gaseous medium with a refractive index lower than that of the fiber to collect an optical spectrum of the sample material.

The spectrum obtained through the optical fiber in contact with the absorbing or emitting medium (sample or analyte of interest) is dependent on the reflection angles (mode structure) of the light beam propagating within the fiber, the refractive indices of the fiber and absorbing medium, and the absorption coefficient of the absorbing medium. Light rays propagating at reflection angles close to the critical angle tend to propagate the evanescent wave further into the absorption medium, while light rays propagating at reflection angles greater than the critical angle are not reflected. Also, higher angle light rays produce more internal reflections per unit length of fiber, thus increasing the sensitivity of the sensor.

Conventionally, the technology uses an unclad sensor portion either by connecting an unclad length of sensor fiber in circuit (for example with optically clad transmission fibers), or by removing (either mechanically or chemically) cladding in the sensor region from a clad fiber while retaining optical cladding in the transmission portion(s) of the fiber. The cladding may be, for example, glass or plastic, and it is difficult to remove such cladding from the core fiber without introducing scattering sites on the core or other distortion introducing aberrations. Also, the interconnection of two fibers, for example, an unclad length of sensor fiber to a length of transmission fiber, frequently introduces loss of signal and signal distortion or noise such as reflections and other aberrations at the connector interface that significantly reduce signal to noise ratios.

In accordance with one aspect of the invention, there is provided a radiation transmission fiber for spectroscopic monitoring that includes a transmission portion and a sensor portion. The transmission and sensor portions have a continuous core portion and continuous cladding over the core portion throughout the transmission and sensor portions. The cladding in the transmission portion is of greater thickness than the cladding in the sensor region, cladding in the transmission region preferably having a thickness sufficient to contain the evanescent field, and in a fiber with a numerical aperture of 0.2, a thickness of greater than about two wavelengths at the radiation wavelength region employed for analysis purposes; while the cladding in the sensor portion is of a thickness such that the evanescent field penetrates into the analytes of interest outside the fiber; and in a fiber with a numerical aperture of 0.2, a thickness of less than between about 0.2 and one wavelength at the radiation wavelength region employed for analysis purposes. The thickness of the cladding in the sensor region may be reduced by etching with a suitable etchant such as potassium hydroxide or hydrogen fluoride, or by mechanical working as by stretching. While the fiber may be as short as one-half centimeter, in a particular embodiment the fiber has a length of at least about one meter and the sensor portion length is less than about five percent of the overall length of the fiber.

The sensor fiber core preferably is of a chalcogenide glass such as arsenic sulfide, arsenic germanium selenide, germanium selenium tellurium, or germanium arsenic selenium tellurium, a heavy metal fluoride glass, fused silica, or polycrystalline or single crystal materials such as thallium, bromohalide, cesium halide or silver halide. Preferably, the sensor core has a diameter of at least fifteen micrometers but less than one millimeter and a refractive index greater than 1.5. Preferably, the fiber includes structure for changing the mode structure of the light beam propagating within the fiber, as by providing a multiturn spiral coil of fiber of relatively small radius or by making the sensor portion of the core of smaller diameter than the transmission portion(s) and connecting the sensor portion to the transmission portion(s) by a conical transition portion(s).

In a particular embodiment, the transmission portion has a chalcogenide glass core of about three hundred micrometers diameter and a cladding layer of chalcogenide glass of about twenty micrometers thickness; the sensor region has a core diameter of about ninety micrometers and a cladding glass thickness of about six micrometers; the sensor region has a length of about eight millimeters; and two tapered transition regions each of about four millimeters length. The optical fiber in the transmission portion has a numerical aperture of 0.22, the glass core has a glass transition temperature of about 250° C., a thermal expansion coefficient of $175 \times 10^{-7}$ per ° C., and a refractive index at 10.6 micrometers of 2.895; while the glass cladding has a glass transition temperature of about 200° C., a thermal expansion coefficient of $177 \times 10^{-7}$ per ° C., and a refractive index at 10.6 micrometers of 2.887. The cladding layer in the sensor region has a thickness of 0.7-1.1 wavelengths of light over a 4-11 micron wavelength range of interest. Such a sensor used as an evanescent sensor has advantages such as avoidance of noise introduced by removing cladding completely mechanically or chemically from the core for an unclad sensor; avoidance of noise and loss of signal introduced by having to connectorize a core only sensor portion to a core/clad transmission portion; avoidance of interfering absorptions of polymeric cladding materials commonly used on core only transmission fibers; avoidance of interfering absorptions of liquid/gas pressure sealing materials; and allowance for easy transition from low order mode light in typical low numerical aperture optic core/clad fiber to high order mode light for evanescent sensing.

In accordance with another aspect of the invention, there is provided a spectroscopy system that includes a source of radiation for generating a beam of radiation, spectrum analyzing apparatus, and an elongated radiation transmission fiber for disposition in an absorption medium comprising a transmission portion and a sensor portion, and coupling structure for coupling the transmission fiber to the source to transmit a beam of radiation through the fiber to the sensor portion and for coupling the fiber to the analyzing apparatus for analyzing the absorption medium in which said sensor portion is disposed. The fiber length may range from less than one centimeter to ten meters or more. The transmission and sensor portions have a continuous core portion and continuous cladding over the core portion throughout the transmission and sensor portions. The cladding in the transmission portion is of greater thickness than the cladding in the sensor region, and preferably the sensor portion of the core is of smaller diameter than the transmission portion and is connected to the transmission portion by a conical transition portion.

BRIEF DESCRIPTION OF THE DRAWINGS

Other features and advantages of the invention will be seen as the following description of particular embodiments progresses, in conjunction with the drawings, in which.

DESCRIPTION OF PARTICULAR EMBODIMENT

Figure 1:
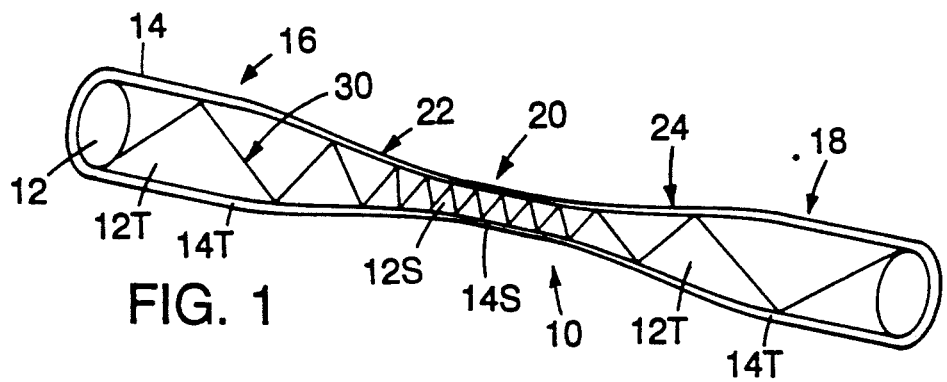
FIG. 1 is a diagrammatic view of an evanescent wave fiber optic sensor in accordance with the invention.

With reference to the diagrammatic view of FIG. 1, optical fiber 10 includes a core portion 12 of germanium, selenium, tellurium chalcogenide glass ($Ge_{25-35}$, $Se_{15-25}$, $Te_{10-60}$) and a cladding layer 14 of similar chalcogenide glass with an added arsenic constituent for lowering the refractive index of the cladding glass ($Ge_{10-25}$, $As_{10-25}$, $Se_{10-40}$, $Te_{20-45}$). Fiber 10 has transmission portions 16, 18, transmission core portions 12T each having an outer diameter of about 295 micrometers and transmission clad portions 14T each having an outer diameter of about 335 micrometers; sensor portion 20 having a length of about seven millimeters, a core 12S of about 88 micrometers outer diameter and cladding 14S of about 100 micrometers outer diameter; and transition regions 22, 24 in which the diameter of the core 12 and the thickness of the cladding 14 change gradually and provide a smooth transition between the transmission portions 16, 18 and the sensor portion 20.

As indicated diagrammatically in FIG. 1, a light ray indicated at 30 propagates at higher reflection angles in the sensor region 20 (tending to propagate the evanescent wave further into the absorbing medium in which the sensor region 20 is disposed) and the smaller diameter sensor region 20 produces more internal reflections per unit length of fiber 10.

Fiber 10 is processed from a unitary clad fiber of cross sectional configuration of the transmission portions 16, 18. The fiber core/clad geometry and amount of drawdown must be carefully controlled to assure containment of evanescent wave in the transmission portion but to allow for propagation through the cladding glass into the analyte of interest at wavelengths of analytical interest in the sensor region. Its ends are secured to tensioning apparatus that applies a low tension to the fiber; the sensor portion is disposed in a silica capillary tube of about 0.5 millimeter inner diameter and a length of about three centimeters which is heated by a low velocity heated air stream until a thermocouple in the air stream adjacent the tube indicates a temperature of at least 320° C. for fifteen seconds. Tension on the fiber is abruptly increased by energizing a stepper motor to stretch the fiber about one centimeter in a fraction of a second to produce a sensor region 20 of reduced diameter and reduced cladding thickness with frustoconical transition portions 16, 18, as diagrammatically indicated in FIG. 1.

Figure 2:
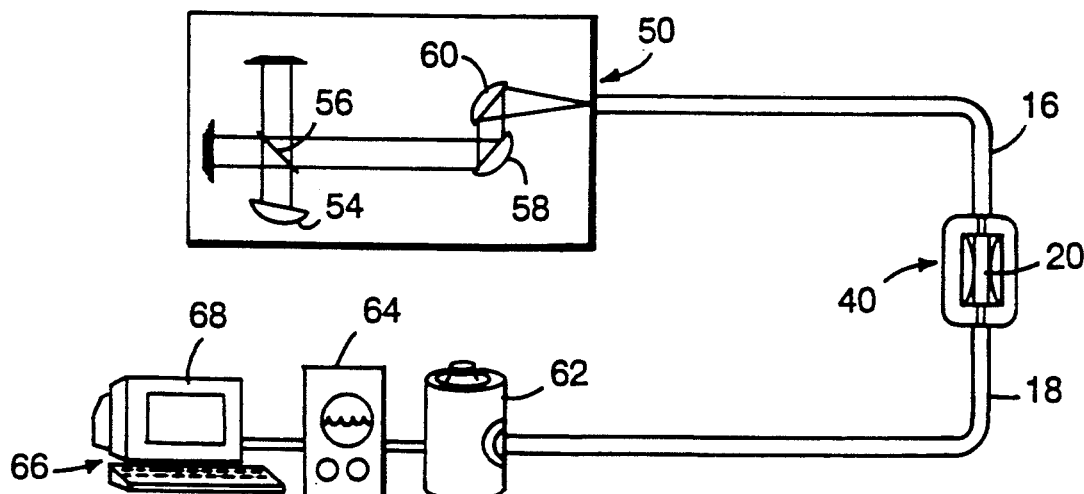
FIG. 2 is a schematic diagram of a spectroscopic system employing the sensor of FIG. 1.

With reference to FIG. 2, the sensor portion 20 of fiber 10 is mounted in polypropylene analysis cell 40 and connected by its transition portions 22, 24 to core clad fiber optic transmission input portion 16 and output portion 18, respectively. Coupled to input transmission portion 16 is an FTIR spectrometer 50 of the Michelson interferometer type that includes infrared source 54, beam splitter 56 and focusing mirrors 58, 60. Coupled to output transmission portion 18 is MCT (mercury cadmium-tellurium) detector 62, lockin amplifier 64 and output processor 66 that includes display 68.

Three solutions of acetone in water at acetone concentrations of 1.0, 0.1 and 0.01 percent, were prepared for analysis by an optical fiber system of the type shown in FIG. 2, thereby giving a 100-fold range of concentrations. The system had a resolution of four wavenumbers. The system was ratioed in air, and then pure (HPLC grade) water was used as a reference in boat 40, and a single beam 256 scan spectrum was run and stored in the processor 66 for reference subtraction. The three samples were then successively run and plotted using 256 scans with the MCT detector 62 and processor 66.

Figure 3:
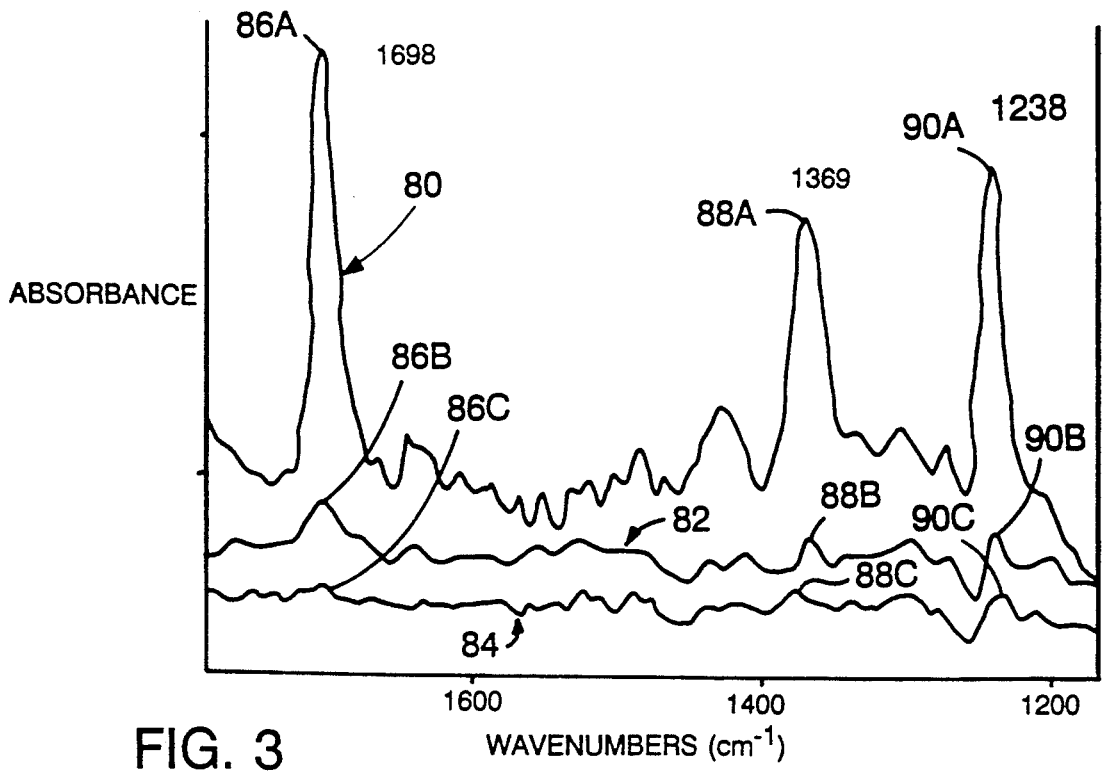
FIG. 3 is a graph of normalized spectra of 1.0 percent, 0.1 percent and 0.01 percent acetone in water obtained with a spectroscopic system of the type shown in FIG. 4.

FIG. 3 shows the 1.0 percent acetone trace 80, the 0.1 percent acetone trace 82 and the 0.01 percent acetone trace 84 (with offset baselines for clarity of presentation). Each trace shows peaks 86, 88, 90 at 1698, 1369 and 1238 wave numbers that are representative of acetone, the one percent 1698 peak 86A being about 6.467 milliabsorbance units, the 1369 peak 88A being about 4.081 milliabsorbance units and the 1238 peak 90A being about 4.854 milliabsorbance units; the peaks 86B, 88B and 90B for the 0.1 percent acetone being about 1/10 of the one percent acetone peaks—that is, the 1698 peak 86B being about 0.772 milliabsorbance unit, the 1369 peak 88B being about 0.329 milliabsorbance units, and the 1238 peak 90B being about 0.389 milliabsorbance units. The 0.01 percent acetone sample had a 1698 peak 86C of about 0.066 milliabsorbance units, a 1369 peak 88C of about 0.034 milliabsorbance units, and a 1238 peak 90C of about 0.039 milliabsorbance units. It will be apparent that a variety of other materials such as the composite materials shown in Stevenson U.S. Pat. No. 4,798,954 may also be analyzed or monitored.

Figure 4:
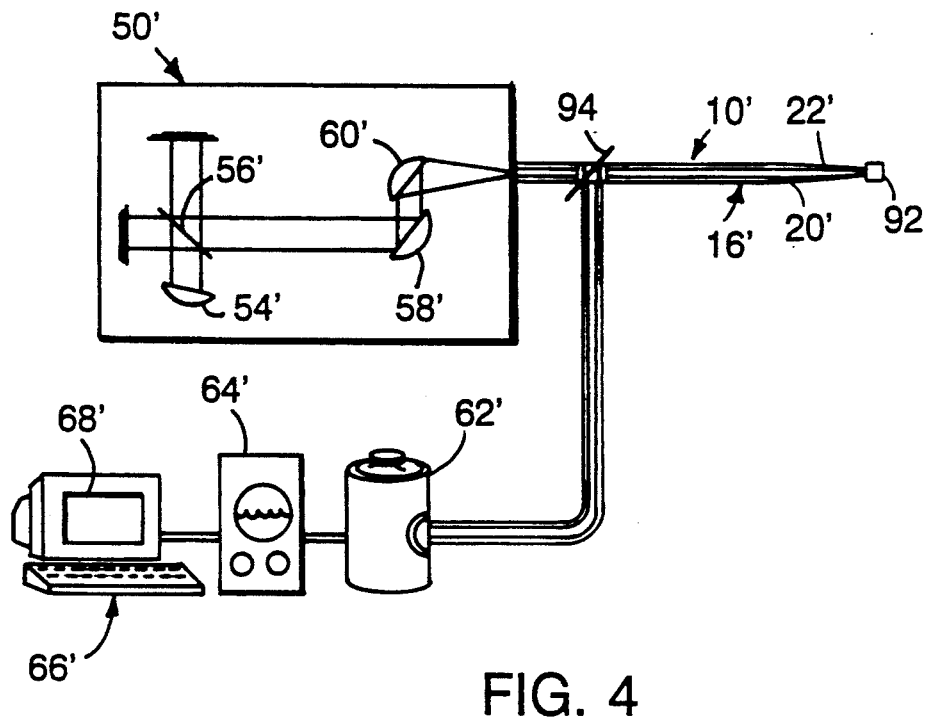
FIGS. 4 and 5 are diagrammatic views of other fiber optic sensor systems in accordance with the invention.
Figure 5:
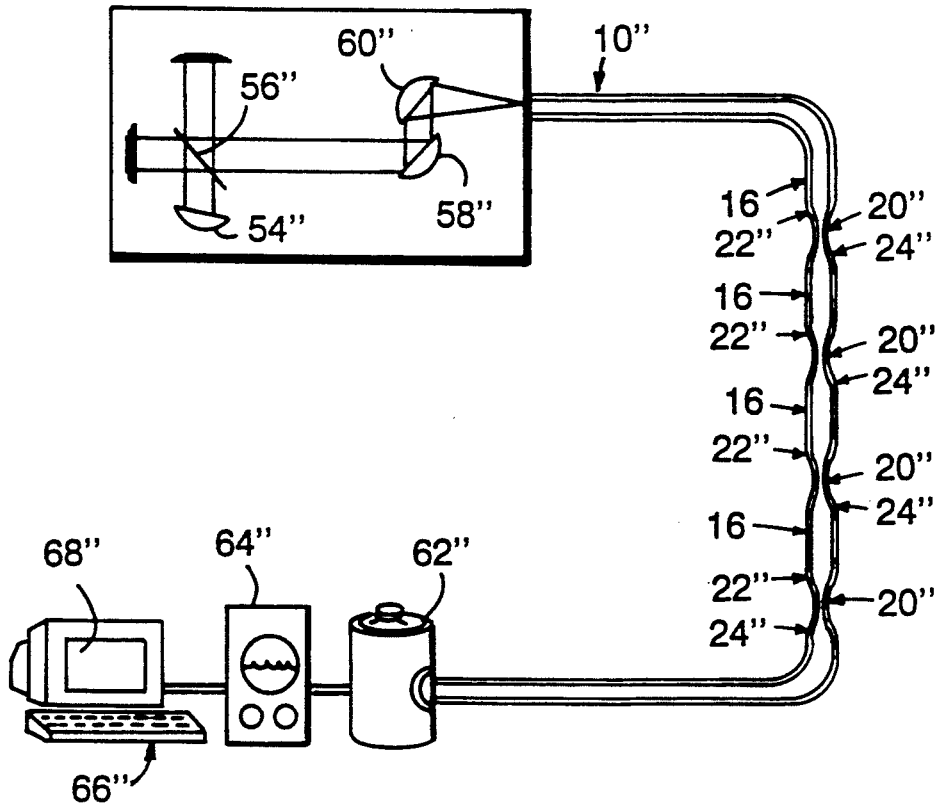

In another embodiment, shown in FIG. 4, the fiber 10 includes a single transmission portion 16' with reflector structure 92 at the remote end of sensor portion 20' so that the transmitted beam as modified by absorbance at sensor 20' is reflected back through portion 16' to a beam splitter 94; and in another embodiment, shown in FIG. 5, the fiber 10" has continuous cladding along its length with a series of sensor portions 20" where the cladding thickness is less than that of the intervening transmission portions 16" and cladding of graded thickness in transition portions 22", 24".

While particular embodiments of the invention have been shown and described, other embodiments will be apparent to those skilled in the art, and therefore, it is not intended that the invention be limited to the disclosed embodiments, or to details thereof, and departures may be made therefrom within the spirit and scope of the invention.

What is claimed is:

1. An elongated radiation transmissions fiber for spectroscopic monitoring comprising a transmission portion, a transition portion of tapered configuration and a sensor portion, said transmission, transition, and sensor portions having a continuous core portion and continuous cladding over said core portion throughout said transmission, transition, and sensor portions, and said cladding in said transmission portion being of greater thickness than said cladding in said sensor portion and the thickness of said cladding in said transition portion changing gradually between the thickness of cladding in said transmission portion and the thickness of cladding in said sensor portions.

2. The fiber of claim 1 wherein fiber has a length of at least about one meter and said sensor portion has a length that is less than about five percent of the overall length of said fiber.

3. The fiber of claim 1 wherein said cladding in said sensor portion has a thickness of less than about one wavelength at the radiation wavelength region employed for analysis purposes.

4. The fiber of claim 1 wherein said cladding in said transmission portion has a thickness sufficient to contain the evanescent field at the wavelengths of analytical interest.

5. The fiber of claim 1 wherein the thickness of said cladding in said transmission portion is at least twice the thickness of said cladding in said sensor portion.

6. The fiber of claim 1 wherein said core is selected from the group comprising chalcogenide glass such as arsenic sulfide, arsenic germanium selenide, or germanium selenium tellurium, heavy metal fluoride glass, oxide glass such as silica glass, and polycrystalline or single crystal materials such as thallium, bromohalide, cesium halide or silver halide.

7. The fiber of claim 1 wherein said sensor core has a diameter in the range of fifteen to one thousand micrometers and a refractive index greater than 1.5.

8. The fiber of claim 1 wherein said transmission portion has a chalcogenide glass core of about three hundred micrometers diameter and a cladding layer of chalcogenide glass of about twenty micrometers thickness; said sensor region has a diameter of about ninety micrometers and a cladding glass thickness of bout six micrometers; the sensor region has a length of about eight, millimeters; and each said tapered transition region has a length each of about four millimeters.

9. The fiber of claim 1 wherein there are a plurality of said sensor portions in series along the length of said fiber, said sensor portions being spaced apart by a series of spaced transmission portions.

10. The fiber of claim 9 wherein said cladding in said transmission portions has a thickness sufficient to contain the evanescent field at the wavelengths of analytical interest, and said cladding in said sensor portions is sufficiently thin to permit the evanescent field to penetrate outside the fiber into the analyte in which the fiber is disposed at the wavelengths of analytical interest.

11. The fiber of claim 1 and further including reflector structure at the end of said sensor portion remote from said transmission portion.

12. The fiber of claim 1 wherein said sensor portion of said core is of smaller diameter than said transmission portion.

13. The fiber of claim 1 wherein said core and cladding have glass transition temperatures within about 100° C. of each other and thermal expansion coefficients within about $1 \times 10^{-6}$/° C. of each other.

14. The fiber of claim 13 wherein said cladding in said sensor portion has a thickness of less than about one wavelength at the radiation wavelength region employed for analysis purposes, and the thickness of said cladding in said transmission portion is at least twice the thickness of said cladding in said sensor portion.

15. The fiber of claim 4 wherein said sensor core has a diameter in the range of fifteen to one thousand micrometers and a refractive index greater than 1.5.

16. The fiber of claim 15 wherein said sensor portion of said core is of smaller diameter than said transmission portion.

17. The fiber of claim 16 wherein said cladding in said sensor portion has a thickness in the range of 0.2-one wavelength at the radiation wavelength region employed for analysis purposes.

18. A spectroscopy system comprising a source of radiation for generating a beam of radiation, spectrum analyzing apparatus, an elongated radiation transmission fiber for disposition in a material of interest comprising a transmission portion, a transition portion of tapered configuration and a sensor portion, said transmission, transition, and sensor portions having a continuous core portion and continuous cladding over said core portion throughout said transmission, transition, and sensor portions, said cladding in said transmission portion being of greater thickness than said cladding in said sensor portion and the thickness of said cladding in said transition portion changing gradually between the thickness of cladding in said transmission portion and the thickness of cladding in said sensor portion, and coupling structure for coupling said transmission fiber to said source to transmit a beam of infrared radiation through said fiber to said sensor portion and for coupling said fiber to said analyzing apparatus for analyzing the absorption medium in which said sensor portion is disposed.

19. The system of claim 18 wherein said source is of the Michelson interferometer type and generates a beam of infrared radiation.

20. The system of claim 18 wherein said analyzing apparatus is of the Fourier transform type.

21. The system of claim 18 wherein said sensor portion is at one end of said fiber, and said source and said analyzer are connected to the same end of said fiber.

22. The system of claim 18 wherein said fiber includes a plurality of said sensor portions in series along the length of said fiber.

23. The system of claim 18 wherein said sensor portion of said core is of smaller diameter than said transmission portion.

24. The system of claim 23 wherein said cladding in said sensor portion has a thickness in the range of 0.2

—one wavelength at the radiation wavelength region employed for analysis purposes.

25. The system of claim 18 wherein said cladding in said sensor portion has a thickness of less than about one wavelength at the radiation wavelength region employed for analysis purposes, and the thickness of said cladding in said transmission portion is at least twice the thickness of said cladding in said sensor portion.

26. The system of claim 25 wherein said core and cladding have glass transition temperatures within about 100° C. of each other and thermal expansion coefficients within about $1 \times 10^{-6}/°$ C. of each other.

27. The system of claim 26 wherein said sensor core has a diameter in the range of fifteen to one thousand micrometers and a refractive index greater than 1.5.

28. The system of claim 27 wherein said core of said fiber is selected from the group comprising chalcogenide glass, heavy metal fluoride glass, oxide glass and polycrystalline or single crystal materials such as thallium, bromohalides, cesium halides and silver halides.

* * * * *